United States Patent [19]

Bonfield

[11] Patent Number: 4,680,394

[45] Date of Patent: Jul. 14, 1987

[54] METHOD OF PREPARING FORMALDOXIME TRIMER

[75] Inventor: John H. Bonfield, Basking Ridge, N.J.

[73] Assignee: Allied Corporation, Morris Township, Morris County, N.J.

[21] Appl. No.: 778,935

[22] Filed: Sep. 23, 1985

[51] Int. Cl.$^4$ ............................................ C07D 251/06
[52] U.S. Cl. ..................................... 544/193; 544/215
[58] Field of Search ................................. 544/193, 215

[56] References Cited

U.S. PATENT DOCUMENTS

| | | | |
|---|---|---|---|
| 4,096,187 | 6/1978 | Bonfield et al. | 260/601 H |
| 4,155,933 | 5/1979 | Bonfield et al. | 260/566 A |
| 4,323,706 | 4/1982 | Bonfield et al. | 564/253 |

OTHER PUBLICATIONS

Mitsubishi Gas Chemical Company, CA, vol. 98, 1983, 98:127089q.
Funaoka et al, CA, vol. 75, 1971, 75: 153143x.
K. A. Jensen, et al. Invest. of Formaldehyde Oximes, Its Polymers and Coord. Cpds. I, Mat. Fys. Med, 40:1, pp. 3-23, (1978).
F. A. Anderson, et al., Invest. of Formaldehyde Oximes, Its Polymers and Coord. Cpds. II, Mat. Fys. Med. 40:2 pp. 3-24 (1978).

*Primary Examiner*—Henry R. Jiles
*Assistant Examiner*—J. G. Mullins
*Attorney, Agent, or Firm*—Harold N. Wells; Jay P. Friedenson; Patrick L. Henry

[57] ABSTRACT

An improved process for preparing formaldoxime trimer is provided in which loss of the product is minimized and the prior art problems of long retention times to afford precipitation of the trimer which is difficult to filter and which occludes the undesirable salt of the acid that is difficult to remove. The method disclosed involved oximation of paraformaldehyde using dehydroxylamine sulfate and ammonia gas followed by steam stripping to recover formaldoxime and separate trimerization thereof followed by filtration recovery and drying.

The formaldoxime trimer is produced in essentially quantitative yield and proceeds specifically by a procedure of steam stripping out the formaldoxime monomer from the synthesis liquor and allowing separate trimer formation and recovery. The product is free from inorganic salts and the mother liquor with formaldoxime monomer content, resulting from its recovery by filtration, does not represent a yield loss in that it is recyclable to the next synthesis reaction.

7 Claims, 1 Drawing Figure

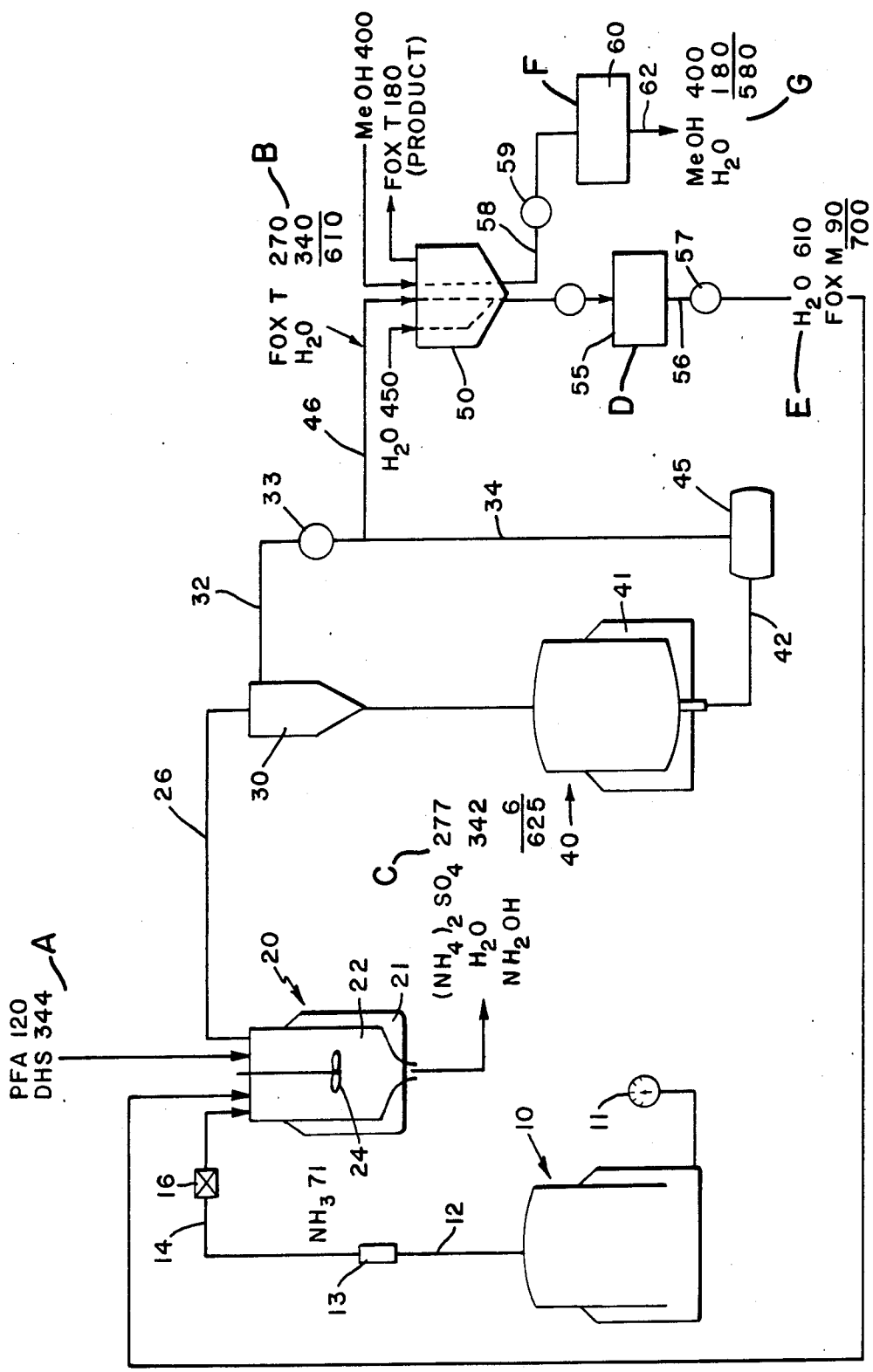

METHOD OF PREPARING FORMALDOXIME TRIMER

This invention relates to an improved method for the manufacture of a formaldoxime trimer.

BACKGROUND OF THE INVENTION

Although formaldoxime, hereinafter sometimes referred to as "FOX-T", is the first and simplest aliphatic aldoxime in the aliphatic series, its manufacture embodies a series of problems which devolve from both the high reactivity of the raw material used in its manufacture, namely, formaldehyde and the tendency of the product formaldoxime monomer (FOX-M) to convert to a formaldoxime trimer (FOX-T). Specifically, formaldehyde exists as a monomer, as polymers and as a trimer, paraformaldehyde; and the product oxime exists not exclusively as the low boiling liquid monomer but also as a high melting solid polymer/trimer.

Formaldehyde exists as the following structures in solution in water: $CH_2(OH)_2$, methylene glycol; poly(oxymethylene glycols), $HO(CH_2O)_nH$; hemi formals of these glycols; HCHO; $-(CH_2O)_n-$; and a cyclic trimer as shown below:

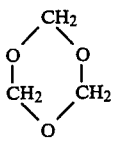

The cyclic trimer may be isolated as a white crystalline powder by concentrating the aqueous solutions. This trimer is an article of commerce.

Generally, methanol is used, 10–15 w % in 35–40 w % aqueous solutions of formaldehyde (HCHO), to inhibit such polymer-trimer formation.

Likewise formaldoxime can exist as a water soluble monomer $CH_2=NOH$ but will rapidly revert to the polymer

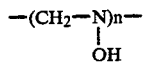

wherein "n" has a variable value; or to the trimer

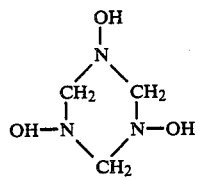

The variable value of "n" is known and discussed in the prior art and as such reference is made, for example to K. A. Jensen and A. Holm, Investigations of Formaldehyde Oxime, Its Polymers and Coordination Compounds, I, Mat. Fys. Med. 40:1, pp. 3–23 (1978), and E. A. Andersen and K. A. Jensen, Investigations of Formaldehyde Oxime, Its Polymers and Coordination Compounds, II, Mat. Fys. Med. 40:2, pp. 3–24 (1978).

The trimer is a high melting solid (MP145°–156° C.); the exact melting point depending on polymer-trimer ratios in the mixture which are believed to exist but which are not readily determinable. The monomer, on the other hand, is a liquid, BP 89° C.

Literature source preparation of the trimer, FOX-T, has involved the addition of formaldehyde to a pre-neutralized aqueous solution of hydroxylamine salt followed by prolonged low temperature storage of the solution to allow precipitation of the formaldoxime trimer which is then recovered by filtration. It has been found that this method results in the formation of a very fine precipiate of FOX-T which adversely blinds the filter device such that recovery is very slow. The solid also occludes large amounts of the salt of the acid entity associated with the hydroxylamine salt which is difficult to remove from the FOX-T without considerable washing and some loss thereof due to some degree of reversion of FOX-T to the formaldoxime monomer FOX-M. There is also direct yield loss due to the presence of the monomer and the reaction of the monomer which has not gone to the trimer in the mother liquor from the primary recovery filtration and the wash.

In the reaction in water, there apparently exists an equilibrium between the trimer and monomer. The formaldoxime monomer stays as the monomer in dilute solution but when formaldoxime monomer reaches 15–20 weight percent, the trimer will start to form. The rate and extent of the trimer formation seem to depend on temperature/pH/time. The lower the temperature, the longer the reaction time and the more the trimer which forms. However, there is always some formaldoxime monomer formation. The higher the pH, the more the amount of monomer which forms.

SUMMARY OF THE INVENTION

In accordance with the method of the invention, the foregoing problems are avoided and essentially quantitative yield of the formaldoxime terpolymer is obtained. The method of the invention proceeds specifically by a procedure of steam stripping out the formaldoxime monomer from the synthesis liquor and allowing separate trimer formation and recovery as described below. In this way, the product is free from inorganic salts and the mother liquor with the monomer (FOX-M) content resulting from its recovery by filtration does not represent a yield loss in that it is recyclable to the next synthesis reaction.

BRIEF DESCRIPTION OF THE DRAWING

In the drawing, a flow diagram is provided illustrating the process of the invention for preparing the formaldoxime trimer and including reference to a typical mass balance of the process reactions.

DETAILED DESCRIPTION OF THE INVENTION

As has been noted, the high reactivity of formaldehyde itself coupled with the spontaneity with which the product oxime reverts to the trimer (FOX-T) introduce a series of special requirements into the successful high yield preparation of FOX-T by the procedure of the invention. This procedure, the details of which are enumerated below, involves the following reaction and is conducted in aqueous solution.

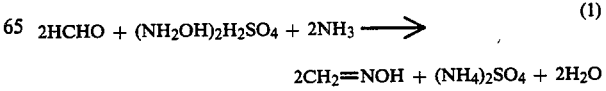

Procedure

1. The formaldoxime reaction 1.1 In the reaction it is preferable to use dihydroxylamine sulfate (DHS) either as is or as is present in standard ammonia process based Rachig hydroxylamine solution and not hydroxylamine hydrochloride as source of the NH$_2$OH entity. This must be coupled with NH$_3$ gas neutralization. The reason for this is that the FOX-M produced is recovered by stream stripping and there is much less free NH$_3$ gas strip on boiling (NH$_4$)$_2$SO$_4$ than in boiling NH$_4$Cl; NH$_3$ going with the FOX-M in the emergent vapor has undesirable effect on trimer formation as described below in 3.3.

1.2 It is distinctly advantageous to use NH$_3$ gas; aqueous NH$_4$OH solution may be used but is not as desirable for reason noted in paragraph 2.2 below. NaOH may not be used. The amount of NH$_3$ gas used must be at least stoichiometric, relative to HCHO used, but substoichiometric, relative to dihydroxylamine sulfate (DHS) used. The amount of DHS used is preferably at least 1.05 mols per 2 mols of formaldehyde (HCHO) (or about 2.1 mol NH$_2$OH per 2 mol HCHO). The reason for this is to avoid free NH$_3$ carry over during steam strip for formaldoxime monomer from the reaction liquor for reason 3.3 below again. Aqueous NaOH or NaOH cannot be used for neutralization in that it leads to severe color degradation of both reaction mass and steam stripped out FOX. The cause of this color degradation is not known, but is probably due to strong base catalysed poly condensation of HCHO and causation of Cannizzaro type reactions as in reaction (2).

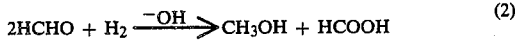

$$2HCHO + H_2 \xrightarrow{-OH} CH_3OH + HCOOH \qquad (2)$$

1.3 It is preferred that paraformaldehyde (PFA) be used as source of formaldehyde, where available, or in lieu thereof, gaseous anhydrous HCHO. The reason for this is that HCHO, as HCHO, is usually available only as 35–40 wt % aqueous solution and the water introduced by use of such solutions upsets process water balance which must be controlled for the reason noted hereinafter in paragraph 2.2. Aqueous HCHO stabilized with methanol should not be used both for the above water balance reason and because methanol progressively detracts from the amount of trimer deposition as in noted in paragraph 3.4 hereinbelow.

1.4 When paraformaldehyde (PFA) is used, it is best added to the dihydroxylamine sulfate solution before NH$_3$ gas addition, and not afterwards, in that the paraformaldehyde PFA is then more easily wetted and dispersed. With PFA, there is no pH inflect on NH$_3$ addition such as attends oximation of almost any other ketone or aldehyde, so NH$_3$ addition must be controlled by weight. The pH inflect on "normal" oximations is due to reaction (1) releasing free H$_2$SO$_4$ which is then neutralized by NH$_3$. In the process of the present invention, the entity HCHO is not instantly present, but is formed gradually during the process of neutralization by de-trimerization of PFA as in reaction (3).

$$(HCHO)_3 \rightarrow 3HCHO \qquad (3)$$

1.5 Where PFA is used, as described in paragraph 1.4 above, the neutralization pH inflect is observable if the mixture is heated to 80°–90° C. to perform reaction (3) and then cooled before NH$_3$ addition. This procedure, however, is not as desirable as that described in paragraph 1.4 above in that yields are lower and the color of the product is not as good.

1.6 If reaction is done via the heating and cooling procedure of paragraph 1.5, there is no FOX-T deposition in the reaction liquor after NH$_3$ gas neutralization. Nor is there any FOX-T deposition if aqueous HCHO is used in the reaction mixture before neutralization. If the reaction is conducted as in paragraph 1.4 or aqueous HCHO is added after NH$_3$ neutralization (when using the procedure of paragraph 1.4, free HCHO formation follows neutralization), FOX-T will precipitate from reaction liquor. Recovery of FOX-T via direct filtration of such reaction liquor results in relatively poor yield, high retention of (NH$_4$)$_2$SO$_4$ in the FOX-T cake and very slow filtration recovery. Poor yield is due to significant FOX-M going in (NH$_4$)$_2$SO$_4$ mother liquor from which recovery, except by steam strip, is difficult.

1.7 The amount of water used in the reaction (either as water or as recycle mother liquor from trimerization (see below) is important. It should be such that after steam strip the residual liquor is optimally saturated at its boiling point with (NH$_4$)$_2$SO$_4$ in that this greatly assists in FOX-M rejection to vapor and allows a higher concentration of FOX-M in the condensed product which in form maximizes FOX-T recovery therefrom and the objectives denoted in 1.8 below.

1.8 Where recycle mother liquor is used in the reaction, the FOX-M content should not exceed about 20w % (optimally 14–15 w %). Otherwise difficulties will arise such as:

the solubility of dihydroxylamine sulfate (DHS) is adversely affected;

a too thick slurry results both from undissolved DHS, undetrimerized PFA and FOX-T. This results in poor NH$_3$ gas distribution and mass/transfer cooling problems; and an intractable foam is generated during the steam stripping of FOX-M.

The system water balance is used to control the FOX-M content in recycle mother liquor.

2. Steam Stripping

With respect to steam strip recovery, both FOX-M and FOX-T in the reaction liquor is recoverable; FOX-T detrimerizes to FOX-M on boiling and is carried over with the steam.

2.1 It is mandatory that the FOX-M-H$_2$O vapors emerging from the reactor on steam strip are not condensed by exposure to cold solid surface as solid FOX-T is formed and will plug the condensing device. The solid FOX-T is essentially insoluble in cold or hot water. It should be condensed, preferably by a medium that is not static, e.g., in a squelch type device wherein it contacts a relatively cool continuously wetted surface such as that described in connection with the drawing. FOX-T is formed but comprises a manageable slurry when done in in this manner. This arrangement to condense the FOX-M can be of any suitable form provided it allows for free circulation of the FOX-T slurry (this excludes use of packed towers or spray nozzles) and that all surfaces where vapor condensation occurs are continuously flush-wetted.

2.2 The process water balance should be such that the weight percent (w %) (NH$_4$)$_2$SO$_4$ left behind after FOX-M strip is in the 40–50 w %, preferably 44 w % range and that the FOX-M in the mother liquor plus wash is no more than 20 w %, preferably 14–15 w % and that the water balance allows the maximum amount of water to be used as displacement cake wash. The optimal mass balance is shown in the drawing.

2.3 During the process of steam strip the reboiler initially boils at 86°–88° C. and the emergent vapor is at 84°–86° C. As the formaldoxime monomer is removed, these temperatures gradually rise. When the reboiler is at 105°–106° C. (44 w % $(NH_4)_2SO_4$ present) and the vapor is at 100° C., all formaldoxime monomer has essentially been recovered. Any FOX-T present as slurry reverts to formaldoxime monomer and is stripped out as such. The progress of recovery accordingly is easily followed and is, at the end, essentially quantitative.

3. Vapor Condensation

The vapor from the reactor/steam stripper is condensed in the manner described above in a squelch condenser primed with initial minimum inventory of water or mother liquor from a previous run which is recycled by a pump as shown in the drawing to a wetted surface device. The recirculating liquor is cooled to 0°–5° C. in an appropriate manner.

3.1 The liquor in the squelch condenser system must be maintained at 0°–5° C. to initiate trimer formation. If this is not done extent of trimer deposition is significantly reduced and gives rise to problems as described, for example, in paragraph 1.8 due to high FOX-M content in mother liquor.

3.2 It is preferable to allow the contents of the trimerizer to be held with recycle for a period of time, for example, of the order of at least 4 hours and more advantageously, 16–20 hours, before filtration is attempted. Where filtration is effected sooner, there will be less cake recovery and filtration will be greatly slowed due to finer crystal being present which block the filter and hinder flow.

3.3 The use of any excess $NH_3$ in the reaction is to be avoided as this can be carried over to the squelch trimerizer and induce rapid, and somewhat unpredictably heavy trimer deposition. This can occur to the point of solidification of the contents of the trimerizer. The amount of FOX-T in the solid is not increased but the crystal is finer and amount of mother liquor retained therein much greater. Filtration recovery is much slower due to the formation of the finer crystal.

3.4 The use of aqueous HCHO solution stabilized with methanol is to be avoided as methanol boils over to the squelch trimerizer wherein it inhibits trimer deposition leading to both FOX-M and methanol build up in the mother liquor which causes problems of the kind noted in paragraph as 1.8. The methanol can be fractionated out of the mother liquor but the process of doing so introduces an additional step and results in the thermal color degradation of the mother liquor. Fractionation separation is not clear cut since once bulk methanol is removed a FOX-M-$H_2O$ azeotropic mixture tends to follow with formaldoxime trimer deposition on the cold solid condensing surface of the conventional still used for its separation.

4. Recovery of Formaldoxime Trimer

The FOX-T after maturation in the slurry as noted in paragraph 3.4 is recovered by filtration. A filter or a centrifuge may be used in the recovery. The cake is sucked or spun until "drip dry". At this point, the cake, even though drip dry, still holds a large amount of mother liquor which is "saturated" with FOX-M (about 20 w %). About 50% of the cake is such mother liquor; this would be lost if an attempt was made to dry it in that state. To remove this mother liquor with its formaldoxime monomer content, a displacement water wash is used. The amount of wash water should be the maximum usable consistent with overall process water balance stipulations as noted by reference to the mass balance described by reference to the drawing, to ensure removal of the formaldoxime monomer. After the water wash, the wet cake now comprises about 50% $H_2O$, but is essentially free of FOX-M.

4.1 The wet drip-dry cake cannot be dried essentially free of $H_2O$ by suction or by vacuum oven or other conventional $H_2O$ evaporative techniques. This is because during such a process there is continuous formaldoxime trimer to formaldoxime monomer reversion and evaporative loss of FOX-M (BP 84° C.) along with the $H_2O$. $H_2O$ content is so high that essentially all formaldoxime trimer is lost by the process of drying in this manner.

4.2 I have found that the preferred way to dry formaldoxime is to use a displacement wash with a volatile compound such as methanol in which water is soluble and in which the formaldoxime trimer is insoluble. When methanol is used to dissolve/displace water, the resultant methanol wet—$H_2O$ dry cake may then be sucked dry. In the process of drying there is an initial rapid weight loss due to methanol evaporation followed by a break in the weight loss curve after which there can be further weight loss due to FOX-T to FOX-M reversion but which is appreciably less than when $H_2O$ is the cause of cake wetness.

The practice of this invention may be further illustrated by reference to the drawing and the examples given below. In figure of the drawing, the use of recycle mother liquor to reaction is illustrated and described. In describing the process, it will be understood that until the reaction has been effected, there is no mother liquor to be processed so a first batch would use instead plain water. Illustratively, 600 parts $H_2O$ are introduced for the first batch stream; at the end of a run series there is 700 parts mother liquor left, which, if discarded, would be a yield loss. The formaldoxime monomer content may be recovered by saturating with $(NH_4)_2SO_4$ and steam stripping out the formaldoxime monomer. The product then yields more formaldoxime trimer and mother liquor (now a lesser amount) which may again be saturated with $(NH_4)_2SO_4$ and stripped. This can be done to "squeeze down" to essentially zero terminal recovery of formaldoxime trimer. In practice, however, this would normally be laborious and impractical beyond a few recoveries.

Referring more specifically to the drawing, in a typical system reactor stripper 20 is charged with water in initiating a first batch. In subsequent batches, recycle is supplied from the mother liquor storage 55. With agitator 24 started, the stripper 20 is charged with proper quantities of dihydroxylamine sulfate and paraformaldehyde. Cooling is provided by the jacket 21. A weighted quantity of ammonia gas is fed from storage tank 10, via line 14 through the flow meter 13, and line 12 using scale 11 to control quantities. The check valve 16 prevents suck back of the reaction liquor from vessel 20 into the ammonia supply 10. The squelch trimerizer 40 is provided with sufficient recycle inventory of either water or mother liquor from a previous batch, cooling is provided for vessel 40 by jacket 41, and recirculation is established by pump 45 via line 42. When recycle flow has been established, the contents of vessel 20 are heated, boiling being initiated at about 85° C. vapor temperature, and FOX monomer is via line 26 condensed as a squelch condensate using the cyclone vessel 30.

The progress of the stripper is followed in that the temperature of the liquid in vessel 20 rises to 104°–105° C. and lines out at that temperature. Vapor temperature rises from 85° C. to 100° C. When the vapor temperature reaches 100° C, all FOX monomer is recovered from the reaction medium. The contents of the vessel 20 may then be cooled and suitably disposed of. This product is essentially ammonium sulfate in water solution at 38–44wt % solids. Meanwhile, the contents of vessel 40 is cooled to 0°–5° C. and allowed to circulate through the cyclone 30, via line 42 using the pump 45 flow control 33 and line 32, for 12–16 hours. This permits maximum development and precipitation of FOX trimer which is an insoluble solid. At the end of this period, the contents of vessel 40 are discharged to filter 50 via line 46 leaving behind only sufficient heel in the vessel 50 to provide for recirculation a squelch condensation of FOX monomer from the next batch.

Alternatively, the contents of vessel 40 may be discharged totally to filter 50 and vessel 40 primed for the next batch with mother liquor from the vessel 55. The FOX trimer cake in filter 50 is washed by a layering displacement wash in water, the amount of water used should preferably not exceed the weight of the cake. This wash water displaces mother liquor (that is rich in FOX monomer) from the cake. This wash is combined in the mother liquor from the initial filtration in vessel 55. The contents of vessel 55 are then recycled to vessel 20 via line 56 and flow control means 57 for the next batch. A part may be recycled to vessel 40 as prime for circulation of the flow in the squelch trimerizer. When the contents of filter 50 are drained fully, the filtrate discharge from the vessel is directed to vessel 60 via line 58 and flow control 59. A displacement wash of methanol is layered onto the cake in filter 50 and drains to vessel 60. This wash serves to displace water in the cake and allows cake drying without the loss of FOX-T which occurs when water wet cake is dried and wherein FOX-T reverses to FOX-M. The loss occurs when attempts are made to dry water wet cake. When dried, such as by passage of air on filter 50, the cake which is pure FOX trimer is appropriately packed out. The methanol water mixture in tank 60 may be fractionated to recover the methanol content therein.

In a typical practice of the recycle process described, reference to the drawing, the material quantities by weight (mass balance), as noted on the drawing as A, B, C, D, E, F, and G, are those experienced in the practice of the process. In this connection, the charge to vessel 20 as shown in the drawing at "A" reflects 120 parts paraformaldehyde, 344 parts of dehydroxylamine sulfate and 700 parts of recycled mother liquor (containing 610 parts water and 90 parts FOX-M) from tank 55. Upon completion of neutralization in vessel 20 with 68–71 parts ammonia from storage 10 steam strip squelch condensation and then trimerization (as noted above), the resultant slurry is delivered to filter 50, as noted at "B", with quantities C being discharged from reaction 20. A displacement wash is used with a quantity of water at D; fed via filter 50, which when combined with mother liquor from primary filtrate, results in quantities E which comprises the recycle to the next batch.

The cake in filter 50 is washed with a quantity (F) of methanol; this results in a methanol-water mixture "G" from which the methanol is recovered.

The invention is further described by reference to the following examples provided for purpose of illustration and not limitation.

EXAMPLE 1

To 344 g dihydroxylamine surface (DHS) in vessel 20 (FIG. 1) is added 120 g paraformaldehyde and 610 g $H_2O$. With agitation and cooling 68 g $NH_3$ gas is passed into the mixture over 20 min. period. The mixture is then heated after 100 g $H_2O$ as prime is placed in the squelch-trimerizer and cooling and recirculation through the wetted surface device 30 is started, using pump 45. At 88° C. the reaction mix starts to boil; vapor is 86° C. Boiling is continued until reboiler reaches 105° C. and vapor line 26 reaches 100° C. (it is stopped when vapor line 26 hits 100° C.). The contents of the reaction vessel 20 625 g (44 w % $(NH_4)_2SO_4$) is disposed of in an appropriate manner. The contents of the recycle squelch trimerizer are held 16 hours and then filtered via 50. The cake is washed with 450 ml $H_2O$ which is combined with mother liquor to give 700 g total saved for recycle to next batch. The cake having a weight of 360 g and is saved for methanol dry-wash.

The above procedure is repeated, recycling the 700 g mother liquor to 20. This time, the wet cake after $H_2O$ wash, with 450 g $H_2O$, is 450 g. This procedure is repeated 10 times to yield 3500 g water wet cake. This cake is then stirred or displacement washed with 5 liters methanol filtered, washed with a further 1 liter MeOH, and sucked dry to yield 1700 g FOX-T dry cake. Theoretical yield is 1800 g. Final mother liquor plus wash is 700 g and contains, by GLC assay 90 g FOX as FOX-M. Yield is quantitative, pure white powdery product MP 154°–155° C.

EXAMPLE 2

A sample of water washed drip dry cake made as in Example 1 is vacuum oven dried at 50°–60° C./150 mm Hg. Abs. Tabulated below is the % weight loss of cake.

| Time Hours | % Cake Left |
|---|---|
| 2 | 96 |
| 4 | 92 |
| 6 | 86 |
| 22 | 48 |
| 32 | 24 |
| 47 | 12.5 |

On Buchner funnel air-suck dry at 20°–21° C. the following weight loss occurred.

| Time Hours | % Cake Left |
|---|---|
| 1 | 94.75 |
| 16 | 84.18 |
| 136 | 73 |
| 184 | 62 |
| 305 | 40.6 |
| 425 | 21 |

The cake for all practical purposes never dries. Azeotropic drying using isopropanol or benzene was attempted. This however, resulted in extensive loss of FOX-T by detrimerization.

The lower phase in the overhead trap was FOX-M in $H_2O$.

When the H₂O content of the washed cake had been displaced with methanol, the following suck-dry weight loss pattern resulted.

| Times Hours | % MeOH Wet Cake Left | |
|---|---|---|
| 0 | 100 | |
| 0.25 | 90.66 | |
| 0.5 | 86 | |
| 0.75 | 79 | |
| 1 | 74 | |
| 1.5 | 64 | |
| 2 | 57 | |
| 2.5 | 53 | ← MeOH Free |
| 3 | 51.3 | |
| 4 | 48 | |
| 5 | 47 | |
| 6 | 46.5 | |

EXAMPLE 3

The procession Example 1 was repeated except that before NH₃ addition, the mixture was heated to 85°–90° C. to detrimerize paraformaldehyde and the resultant clear solution cooled to 20° C. before NH₃ addition. 10 cycles produced 1325 g off (tan) colored methanol dried cake. Yield, including 90 g in final mother liquor ws 78.6%. The ammonium sulfate phase left after stream strip was brown colored. Normally, it is water clear.

EXAMPLE 4

(Comparative)

The process as in Example 1 was repeated except an excess (80 g) of NH₃ gas was used in the first batch. The contents of the squelch trimerizer solidified on ~5 hour hold and had to be scraped out. This exemplifies the deleterion effect NH₃ has on trimer formation.

EXAMPLE 5

(Comparative)

The process as in Example 1 was repeated using 344 g DHS, 120 g PFA, at 20° C. slow addition of 800 g 20 w % NaOH solution. The resultant liquor was yellow and on steam distillation, turned black. The FOX-T slurry was dark brown and trimer recovered by filtration brown in color.

EXAMPLE 6

(Comparative)

The process essentially as in Example 1 was repeated except 329 g 37 w % aqueous HCHO solution containing 11 w % MeOH stabilizer was used.

329 g of such aqueous formaldehyde is added to 344 g DHS in 400 g H₂ in vessel 20. Upon addition of 71 g NHg gas from C-1, with cooling, the pH is 4.0. After steam strip to R-2 as in Example 1, is held at 0°–5° C. in R-2 for 20 hours, the wet washed cake is 277 g. Mother liquor and wash H₂O is recycled to next batch in R-1 along with 329 g 37 w % HCHO as above and 344 g DHS. A second wet cake is only 350 g. The amount of cake progressively diminishes as the methanol in the recycle mother liquor builds up. At the end of 10 batches, total wet cake is only 2000 g, dry product 1000 g and amount of mother liquor has ballooned to beyond what can be tolerated with respect to further cake recovery. The above recovery is only a 56 % yield and is progressively diminishing.

It will be apparent that various modifications apparent to one skilled in the art may be effected in the invention herein disclosed without departing from the scope of the invention. Accordingly, the various details disclosed as illustrative are not to be construed as limitations on the invention except as may be recited in the appended claims.

What is claimed is:

1. A process for the manufacture of formaldoxime trimer which comprises:
    (a) reacting formaldehyde, as paraformaldehyde to the substantial exclusion of aqueous formaldehyde, with a slight stoichiometric excess dihydroxylamine sulfate;
    (b) treating the reaction product of step (a) by adding ammonia at least stoichiometrically equivalent to the paraformaldehyde and substoichiometric relative to the dihydroxylamine sulfate;
    (c) steam stripping the reaction product of step (b) to recover the formaldoxime as a vapor; and
    (d) squelch condensing the emergent vapor from step (c) on a continuously flush wetted condensing surface; and
    (e) generating the formaldoxime trimer by cooling the condensate of step (d) to 0°–5° C.

2. The process of claim 1 wherein the dihydroxylamine sulfate is added in step (a) in a stoichiometric excess relative to the paraformaldehyde of at least about 5 percent.

3. The process of claim 1 wherein the ammonia added to step (b) relative to the dihydroxylamine sulfate is at least about 5 percent below the stoichiometric equivalent.

4. The process of claim 1 wherein the formaldoxime trimer in step (d) is generated by means of contact of the vapors on a continuously agitated wetted surface.

5. The process of claim 1 wherein the trimer formation in step (d) is aided by cooling the trimer to a temperature of about 0° C. to about 5° C.

6. The process of claim 1 wherein the formaldoxime trimer product derived in step (d) is dried by displacement wash with methanol and then sucked methanol dry.

7. The process of claim 1 wherein said ammonia is non-aqueous.

\* \* \* \* \*